United States Patent [19]

Green et al.

[11] 4,016,036
[45] Apr. 5, 1977

[54] PROCESS FOR SERIALLY CULTURING KERATINOCYTES

[75] Inventors: Howard Green, Brookline; James G. Rheinwald, Cambridge, both of Mass.

[73] Assignee: Massachusetts Institute of Technology, Cambridge, Mass.

[22] Filed: Nov. 14, 1975

[21] Appl. No.: 632,037

[52] U.S. Cl. .............................................. 195/1.8
[51] Int. Cl.$^2$ ........................................ C12K 9/00
[58] Field of Search .................................... 195/1.8

[56] References Cited

OTHER PUBLICATIONS

Willmer—Cells and Tissues in Culture vol. 2 (1965) pp. 656 and 657.

*Primary Examiner*—Sam Rosen
*Attorney, Agent, or Firm*—Arthur A. Smith, Jr.; Martin M. Santa; David E. Brook

[57] ABSTRACT

A method is disclosed for serially culturing keratinocytes such as human epidermal cells and teratomal keratinocytes. These can be serially grown in culture to produce colonies and eventually stratified squamous epithelium by including in the culture fibroblast cells or medium harvested from fibroblast cultures. When fibroblast cells are used, they are treated to prevent their multiplication, and they are also introduced into the cultures at a controlled density.

27 Claims, 2 Drawing Figures

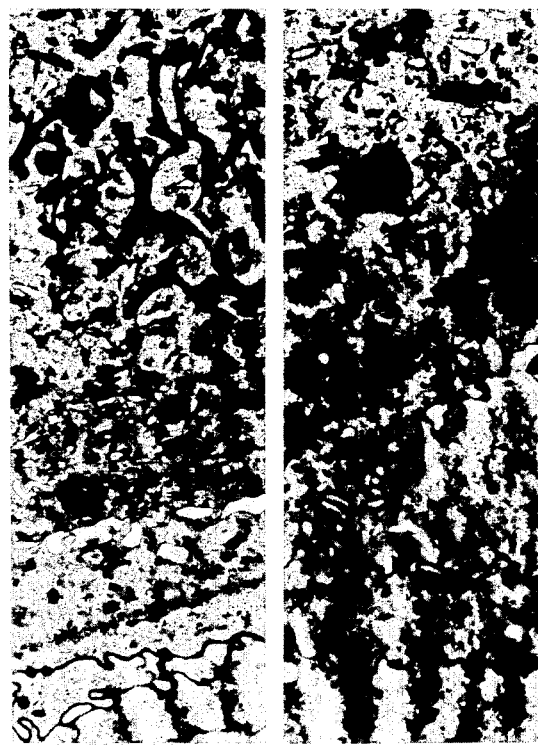
Fig. 1 - Serially Cultured XB Clonal Cells
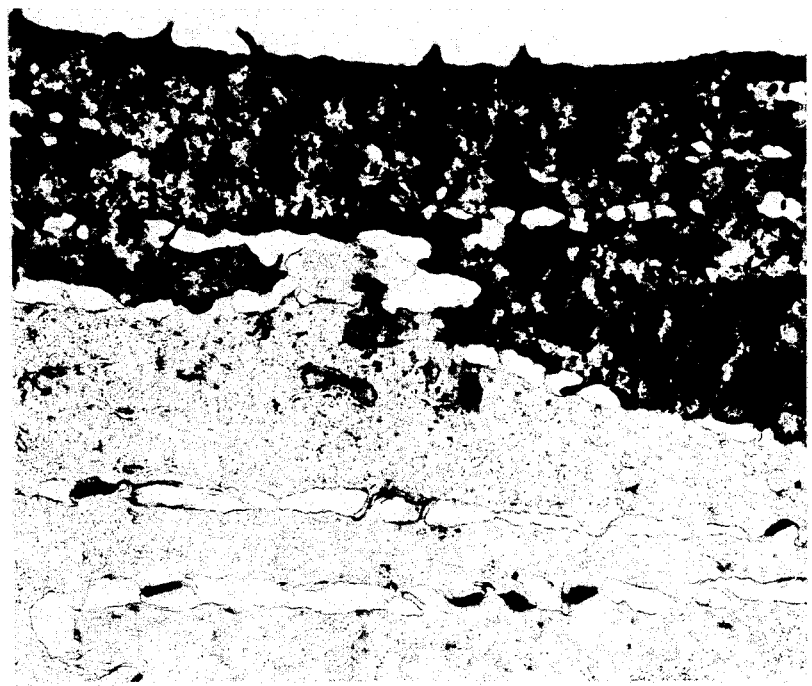
Fig. 2 - Serially Cultured Human Epidermal Cells

PROCESS FOR SERIALLY CULTURING KERATINOCYTES

GOVERNMENT SPONSORSHIP

The invention described herein was made in the course of or under grants from the National Institute of Health.

BACKGROUND OF THE INVENTION

1. Field of the Invention

This invention is in the field of biology and more particularly in the field of cell biology.

2. Description of the Prior Art

Keratinocytes are a cell type which synthesize keratin and are able to form a stratified squamous epithelium. The most common keratinocytes are epidermal cells of the skin. Others include the cells lining the mouth, esophagus or vagina.

Although some types of mammalian cells have been serially cultivated, many mammalian types have continued to resist attempts at serial cultivation, and mammalian epidermal cells are among the latter. Although they have been grown for brief periods in primary culture, all known attempts to serially culture them have been unsuccessful. Some of the numerous literature descriptions of the cultivation of disaggregated epidermal keratinocytes in monolayers are: F. L. Vaughan and I. A. Bernstein, *J. Invest. Derm.*, 56, 454 (1971); M. A. Karasek and M. E. Charlton, *J. Invest. Derm.*, 56, 205 (1971); N. E. Fusenig and P. K. M. Worst, *J. Invest. Derm.*, 63, 187 (1974); and S. H. Uspa, D. L. Morgan, R. J. Walker and R. R. Bates, *J. Invest. Derm.*, 55, 379 (1970).

From studies of explants or short term disaggregated cell cultures, it is known that epidermal cells depend on mesenchymal cells of dermal fibroblasts for survival and growth. See J. W. Dodson, *Exp. Cell Res.*, 31, 233 (1963); N. K. Wessells, *Exp. Cell Res.*, 30, 36 (1963); and A. A. Moscona, *In the Epidermis*, Montagna et al., eds., 83 (1964). Despite such knowledge, fibroblast cells have not been successfully utilized to grow epidermal cells. In fact, because fibroblasts have invariably overrun epidermal cells in mixed cultures, investigators have usually attempted to isolate epidermal cells from fibroblasts and to grow them alone. Very little growth has taken place in such systems.

Because serial cultivation of epidermal cells has heretofore not been accomplished, it has simply not been possible to produce epidermal cells in quantity. Having to depend on skin biopsies for such cells has understandably been a severe restriction on their availability. In addition, the substitutes for epidermal cells used in such applications as covering denuded skin areas on burn victims and in the dermatological screening of drugs have not been satisfactory and suffer from many deficiencies. None of the substitutes used function entirely like natural human epidermal cells.

DESCRIPTION OF THE INVENTION

It has now been discovered that keratinocytes can be serially cultivated under very specific and controlled conditions. Human epidermal cells or other keratinocytes are grown in cultures with fibroblast cells treated to prevent their multiplication. Fibroblast cell density has to be carefully controlled in these cultures to allow epidermal cell colony formation and growth. It has also been found that keratinocytes can be grown in the presence of fibroblast cell products as well as in the presence of the fibroblast cells themselves.

Using the techniques described herein, both teratomal keratinocytes and human epidermal cells have been serially cultured successfully. The number of human epidermal cells can, for example, be expanded from the number in primary culture by many fold, sometimes up to $10^6$ fold or more.

Teratomal keratinocytes have been serially cultured beginning with a clone (XB) which was isolated from a transplantable mouse teratoma. Serial cultivation of these clonal cells produced stratified squamous epithelium.

Teratomas have been studied extensively for differentiation and there have been numerous attempts to adopt such tumors to cell culture conditions. Variable amounts of differentiation have led to the development of established cell lines which do not possess the pluripotentiality of the stem cell of the teratoma, but did possess functions characteristic of known differentiated cell types. See, for example L. J. Kleinsmith and G. B. Pierce, Jr., *Canc. Res.*, 24, 1544 (1964); and M. D. Rosenthall, R. M. Wishnow and G. H. Sato, *J. Nat. Canc. Inst.*, 44, 1001 (1970). One established line derived from cervical carcinoma and adapted to growth in suspension was found to have some ultrastructural features in common with those of keratinocytes.

Despite such prior work, no line having the characteristics of clone (XB) has been described previously. A deposit of this new clonal cell line has been made with the American Type Culture Collection (ATCC) which has assigned number CL-177 to it.

Although this description relates specifically to XB clonal cells isolated from mouse teratomas, it is believed that other teratomas, such as human teratomas, could also be used in the isolation of clonal keratinocytes capable of serial cultivation.

The presence of either fibroblast cells or fibroblast cell products, which can be supplied from medium harvested from fibroblast cultures, is essential to support growth of keratinocytes. While the exact mechanism of operation for the fibroblast cells or cell products is complex and little understood, it does appear that they serve the following functions. Firstly, fibroblasts or their products are necessary for growth and differentiation of keratinocytes. Secondly, if the tissue containing the keratinocytes also contains viable fibroblasts, their multiplication can be suppressed by non-growing fibroblasts — of course, fibroblast cell products are not sufficient to perform this function.

Suitable fibroblast cells include, but are not limited to, 3T3 mouse fibroblasts and human diploid fibroblasts. Of these, 3T3 cells are preferred because they appear to support keratinocyte growth more effectively and because they appear to suppress viable fibroblasts more effectively.

Fibroblast cells are treated prior to inoculation into the epidermal cultures to prevent their multiplication. An efficient way to accomplish this is to irradiate the cells with ionizing radiation such as X or gamma rays until the cells ability to produce progeny is destroyed. Irradiation procedures are known, and one suitable technique is described by T. T. Puck, P. I. Marcus, and S. J. Cieciurra, at *J. Exp. Med.*, 103, 273 (1956). A typical dosage of gamma rays to produce such an effect is about 6000 rads. Irradiated fibroblasts are living in the sense that they still carry on cell metabolism and synthesis, but such irradiated cells lose their ability to multiply although a few may go through one or two divisions.

Alternatively, fibroblast cell multiplication can be prevented by other methods such as ultraviolet irradiation or treatment with compounds which damage DNA such as alkylating agents or mitomycin-C. Those skilled in the art will know others. In fact, any treatment of the fibroblast cells is sufficient if it prevents cell multiplication as described above.

Fibroblast cell density in the keratinocyte cultures must be carefully controlled. It must be sufficiently high to support keratinocyte multiplication and differentiation, on the one hand, and yet on the other hand, it must also be low enough to permit expansion of keratinocyte colonies as the cells grow. In this work, human epidermal cells were inoculated at a density of between about 50 and 5000 cells/cm$^2$ whereas cultures of clone XB cells were inoculated at densities up to about 50 cells/cm$^2$. These are based on practical working levels since the plating efficiency of human epidermal cells tends to be only about 1% whereas the teratoma clone tended to have a plating efficiency of about 40%. For human epidermal cells, 3T3 cell density should be between about 15,000 to about 50,000 3T3 cells/cm$^2$. For culturing mouse teratoma clone XB cells, the preferred 3T3 cell density is up to about 15,000 cells/cm$^2$ because higher density inhibits colony expansion.

Actual contact with fibroblast cells is not necessary for growth and keratinization in all cases. It was found, for example, that XB clonal cells could be supported by mouse fibroblast 3T3 cells located some distance away in a culture dish. XB cells were also able to form colonies and keratinize in the absence of 3T3 cells if the growth medium was previously conditioned by 3T3 cells. Conditioning was achieved, for example, by exposing saturation density cultures of 3T3 cells to medium for 1 day. The medium was then removed and filtered.

Art-recognized cell culture media are suitable for culturing epidermal cells as described herein. Generally, these are synthetic formulations designed to provide sources of amino acids, vitamins, glucose, etc. to the growing cells. Typical culture media suitable for serially culturing epidermal cells are Eagle's medium, the Dulbecco-Vogt modification of Eagle's medium, and Ham's medium. Usually, serum supplement is added to the medium to provide certain proteins, and suitable examples of serum supplements include calf serum and fetal calf serum with 20% fetal calf serum being about optimal.

The keratinous nature of the serially cultivated XB clone was substantiated by several techniques. Following fixation and staining with Rhodanile blue, a mixture of Rhodamine B and Nile Blue, colonies of XB cells stained red at their interior whereas most animal tissues stain blue. The ability of a colony to stain red with Rhodanile blue was very well correlated with the presence of stratified squamous epithelium demonstrable in sections through the colony. Colonies were fixed in the petri dish and cut out of the dish with a saw. The plastic was dissolved in xylene and colonies were embedded in paraffin, sectioned vertically and stained with hematoxylin and eosin. Such colonies were thus shown to really consist of stratified squamous epithelium composed of multiple cell layers. Even a small amount of histologically identifiable differentiation was detected by Rhodamine B alone, indicating that this dye is a very sensitive indicator of keratinization.

Confirmation of the keratinous nature of XB colonies was also obtained by electron microscopy, and FIG. 1 shows two typical electron micrographs actually obtained.

XB cells at 30 cell generations were analyzed after their isolation and found to be heteroploid. Their modal chromosome number was 76, and the range was quite narrow ($\pm 2$).

In most experiments in which XB colonies were trypsinized and the cells inoculated together with $n/3$ 3T3 cells, the plating efficiency was on the order of 40%. This indicates that many cells in even large XB colonies preserve viability and can initiate colony formation.

Studies by radioautography of sections through large colonies (>1,000 cells) showed that many nuclei had incorporated H$^3$ tagged thymidine. The nuclei which did not label were usually located in the most superficial layers of the most stratified part of the colony and were often flattened. The conversion of the keratinocyte to a nondividing and differentiated end stage cell in the colony therefore tends to follow the pattern resembling a stratified squamous epithelium in vivo.

The following properties of the XB keratinizing line suggested a differentiated state similar to that of epidermis or related epithelia: stratification of the cells in colonies; keratinization, as indicated by staining with Rhodanile blue and by light microscopy of sections; ultrastructural features of epidermal cells such as abundant tonofilaments, some keratohyalin granules, and many desmosomes between adjacent cells; and loss of ability to replicate DNA by some nuclei in the stratified layers.

In colonies of human epidermal cells and 3T3 cells, round cells could be seen on top of the 3T3 layer a few days after inoculation. These may have been epidermal cells but keratinocyte colonies could be definitely identifiable only later, after the cells made contact with the dish surface and adopted a typical epithelial pattern. This was easily seen as soon as 4 days after inoculation, when the colonies were quite small. In contrast to the teratomal keratinocyte line, the human epidermal keratinocytes, even at this early stage, were in close contact with each other, and began to stratify. As the colonies grew laterally, the centers thickened and the cell boundaries became difficult to discern. The centers eventually acquired a crackled appearance. All human epidermal keratinocyte colonies stained red with Rhodamine B even though they were very small, whereas the teratomal keratinocyte colonies usually stratified and stained red only when the colonies were large.

Electron micrographs of sections through the colonies confirmed the stratified construction, the keratinization, which was most advanced in upper cell layers, and the abundant desmosomes in all layers. The appearance resembled that of epidermis, and all cells belonged to the same type — keratinocytes. Though they were flattened, the cells closest to the petri dish surface corresponded most closely to the germinative cells in normal epidermis, for cell division in stratified colonies takes place mainly in the deepest layers. FIG. 2 is a typical electron micrograph of human epidermal cell colonies.

Colonies containing over 1,000 cells were labelled for 1 day with H$^3$ tagged thymidine and covered with photographic emulsion. Radioautography showed that the nuclei close to the perimeter of the colonies produced abundant grains but those in the interior of the colonies showed very faint density or none at all. When the same cultures were labelled with $C^{14}$-thymidine, many nuclei in the internal regions of the colonies were labelled. These nuclei were presumably so deep within the colony that $\beta$ particles emitted from tritium could not reach the emulsion; but even after exposure to $C^{14}$-thymidine, unlabelled nuclei could be seen in large flattened cells with thickened cell membranes in the superficial layers of the thicker colonies. These nuclei appeared to belong to cells in the process of differentiation into squamous. Radioautographs of cross sections of large colonies labelled with tritiated thymidine showed that in areas where stratification had occurred, no labelled nuclei were present in the upper layers.

The plating efficiency of human keratinocytes was variable but always considerably lower than that of XB teratomal keratinocytes. Usually, the number of keratinocyte colonies produced by primary disaggregated skin cells was 0.1–1.0%. Even on subculture, the plating efficiency was only occasionally as high as 10% and was usually 1–5% for newborn donors. Toward the end of their culture life the epidermal keratinocytes of both newborn and older donors plated with an efficiency considerably below 1%.

One agent which was found to increase the plating efficiency of human epidermal cells is epidermal growth factor (EGF). EGF was discovered in 1962 in work related to examining the mouse submaxillary gland for the presence of nerve growth factor. S. Cohen, "Isolation of a Mouse Submaxillary Gland Protein Accelerating Incision Eruption and Eyelid Opening in the New-Born Animal", *J. Biol. Chem.*, 237, pp. 1555–62 (1962). EFG has since been found to be a 6000 molecular weight polypeptide of 53 amino acids, lacking alanine, phenylalanine, and lysine. C. R. Savage, T. Inagami and S. Cohen, "The Primary Structure of Epidermal Growth Factor", *J. Biol. Chem.*, 24F, 7612–21 (1972) and C. R. Savage and S. Cohen, "Epidermal Growth Factor and a New Derivative. Rapid Isolation Procedures and Biological and Chemical Characterization", *J. Biol. Chem.*, 24F, 7609–11 (1972). The teachings of these references are hereby incorporated by reference. Adding EGF to cultures of human epidermal cells in concentrations of about 1 to 30 nanograms/ml raises the plating efficiency in subsequent transfers by about 3–10 fold. No similar effect was detected for plating efficiency of teratoma XB clones.

The average doubling time of the XB line of teratomal keratinocytes was about 19 hours. Human epidermal keratinocytes in primary or subsequent culture had a doubling time of about 32 hours over the period from the time of inoculation to the development of colonies containing an average of about 1,000 cells. Since this includes their period of attachment, it is likely that the doubling time in the exponential phase is appreciably shorter. The growth rate of the keratinocytes did not seem to change much on serial subculture until close to the end of their culture life, when it declined sharply.

The keratinocyte strains initiated from humans at different ages from birth to 34 years showed finite culture lifetimes; all grew for at least two transfers, but none grew through more than six.

Human keratinocytes were found to have the diploid number of chromosomes.

Hydrocortisone has been reported to hasten keratinization in skin explants. In intact animals, it is thought to suppress epidermal growth. Because of this, the effect of hydrocortisone on serial cultivation of human epidermal cells was studied.

When the cell suspension obtained from a skin biopsy was plated with 3T3 cells, no difference in growth rate or morphology was observed in the colonies growing in the primary culture if hydrocortisone was added. In secondary and subsequent cultures, however, it was found preferable to include at least about $0.03\mu g/ml$ hydrocortisone in order to initiate orderly, stratified squamous colonies. In its absence, colonies arose at the same frequency, but the cells were elongated, of a more fibroblastic appearance, and a larger clump of cells formed during colony initiation before expansion along the surface of the dish began. After a variable period, when the colonies became larger, part or all of each colony adopted the normal stratified epithelial morphology. The entire colony always stained with Rhodamine. Since initial colony expansion was retarded in the absence of hydrocortisone, the average growth rate of the keratinocytes during each passage was less than when hydrocortisone was included. Above about $10\mu g/ml$, cell growth was suppressed. Because of this, it was preferred to use between about $0.03\mu g/ml$ to $10\mu g$ in cultures of human epidermal cells to improve colony growth and morphology in secondary and subsequent colonies.

The process for serially culturing keratinocytes described herein is useful, of course, for producing epidermal cells. Such cells could be used to cover denuded areas in the treatment of burns and could also be used for drug testing since large numbers of compounds are screened for their dermatological properties.

The invention is further illustrated by the following examples.

EXAMPLE 1

Establishment of Cell Lines from a Transplantable Teratoma

The solid, transplantable teratoma No. 69691 was originated by Dr. L. C. Stevens by grafting a 6 day embryo onto the testis of an adult CXBGB/By mouse. See L. C. Stevens, "Developmental Biol.", 21, 364 (1970). This tumor was carried for 2 years in his laboratory by subcutaneous injection of minced tumor fragments into isologous mice, and produced a wide range of tissue types including nerve, glands, muscle, cartilage and bone. A mouse bearing this tumor was used.

The tumor was minced and disaggregated in 0.25% trypsin, and the freed cells were planted at high density, grown to saturation, and subcultured, again at high density. Teratoma cultures were grown in fortified Eagle's medium supplemented with 20% fetal calf serum and the medium was renewed twice weekly. When the secondary culture reached confluence, most of the cells were clearly fibroblasts, but some nonfibroblastic cells were present on top of the fibroblast layer. A 2 minute incubation with 0.05% trypsin released many of these cells, but only a few fibroblasts. The detached cells were plated in a 15 mm petri dish. Two weeks later, 5 colonies of small epithelial cells could be seen, growing with a doubling time of about 24 hours. At 3 weeks, when the colonies had grown to several hundred cells, the culture was trypsinized and transferred at 1:4 dilution. This was repeated several times. At the end of 6 weeks, more than 80% of the cells retaied their original epithelial appearance. This line was designated XA1.2. Numerous clones were later isolated (XB, etc). This family of cell lines was grown through over 100 generations in culture.

EXAMPLE 2

Use of an Irradiated 3T3 Layer to Support the Growth of the Teratoma Cells and Suppress Fibroblast Growth 3T3 cells were lethally irradiated as follows. Confluent cultures grown in fortified Eagle's medium supplemented with 10% calf serum and containing $3 \times 10^6$ cells in 100 mm dishes were given a gamma-ray dose of 6,000 rads in 35 seconds in a cobalt source.

Monolayers of lethally irradiated 3T3 were trypsinized, and the cels were inoculated at about one-third saturation density ($1.6 \times 10^4$ cells/cm$^2$ or "$n/3$") together with XA1.2 cells in fortified Eagle's medium supplemented with 10% fetal calf serum. The XA1.2 cells appeared to begin growth on top of the 3T3 layer, but very soon made contact with the surface of the culture dish by burrowing between the 3T3 cells. Epithelial colonies were formed with a plating efficiency of about 40%. These colonies expanded on the surface of the dish, pushing the 3T3 cells away at the perimeter. After two serial colony isolations with $n/3$ 3T3, clones were free of contaminating fibroblasts.

EXAMPLE 3

Isolation of Keratinizing Clones and their Detection with Rhodanile Blue

300 XA1.2 cells were plated in a 100mm dish with $n/3$ 3T3 cells in Eagle's medium containing 20% fetal calf serum. Two weeks later a thick colony with a weblike layer over its center was isolated (clone XB) and replated with 3T3 cells. Most of the colonies arising from this clone had the same appearance in the living state, but fixation and staining with Rhodanile blue produced a red stain. Most animal tissues stain blue, but keratinized epithelium stains red.

Staining was accomplished by fixing cultures in 10% formalin in isotonic phosphate buffer and staining for 30 minutes with Rhodanile blue prepared by mixing equal volumes of 2% Rhodamine B and 2% Nile Blue. Cultures were then destained with water until the blue color disappeared from the centers of the colonies, usually in about 2 minutes.

An 18 day culture was developed from 200 XB cells plated with $n/3$ 3T3 cells. After staining, the interior of most colonies stained red, and the outer rim and the 3T3 cells stained blue. Using the two components of the stain separately in other cultures, the Rhodamine B stained only the interior of the colonies, and Nile Blue stained the periphery and the 3T3 background. Thus, Rhodamine B could be used alone to identify keratinizing colonies.

In order to be more certain of the specificity of the Rhodamine B as applied to cell cultures, the staining properties of colonies of well known culture lines of other than epidermal origin was examined. 3T3, 3T6, SV40, a polyoma virus transformant of 3T3, HeLa, human diploid fibroblasts, L-cells, V79, H4IIEC$_3$, HTC, BRL and 4 other teratoma lines with morphology different from XB were plated at low density both with and without $n/3$ 3T3. The rusulting colonies, whether thick or thin, stationary or growing, gave only a blue color after staining with Rhodanile blue.

The correlation between the ability of a colony to stain red with Rhodanile blue and the presence of a stratified squamous epithelium demonstrable in sections through the colony was established as follows. Culture dishes were fixed in Van de Grift's fixative or 10% formalin, rinsed with 95% ethanol, dehydrated with 100% ethanol and permeated with cedarwood oil. Individual colonies were cut out of the dish with a Dremel "Moto Tool" fitted with a sanding wheel, the plastic of the dish was dissolved in xylene, the colony repermeated with cedarwood oil, embedded in paraffin at 60° C, then cut in cross section at 5 or 10 microns. The sections were then stained with hematoxylin-eosin and photographs were taken on Kodachrome, Ektachrome or Kodacolor film. These pictures showed that each such colony really consisted of a stratified squamous epithelium composed of multiple cell layers. Even a small amount of differentiation histologically identifiable in sections was detected by the Rhodamine B staining of intact clones, indicating that the dye is a very sensitive indicator of keratinization. The cells closest to the plastic surface were most analogous to basal cells and the upper layers were usually more keratinized. These colonial epithelia were less well organized than those derived by similar methods from normal human skin, and in some parts their appearance suggested neoplastic change. There was no evidence of the 3T3 cells in the sections, confirming the impression gained from the living cultures that the XB cells displace the 3T3 cells from the surface of the petri dish as the colony expands. Each epithelium formed as a colony is therefore the result of the differentiation of the descendants of a single XB cell.

XB cells produced no tumors in isologous or athymic mice, even when 10$^7$ cells were injected.

XB cells analyzed at 30 cell generations after their isolation were found to be heteroploid. The modal chromosome number was 76, and the range quite narrow ($\pm 2$).

Corroboration of the keratinous nature of the colonies, and of their formation of a tissue resembling epidermis was obtained by electron microscopy. Cultures were washed, fixed in 2% glutaraldehyde, postfixed in 1% osmium tetroxide, and prestained in 1% uranyl acetate. The cultures were then embedded in araldite-epon, and cut in 500A sections. The sections were stained with 2% uranyl acetate and Reynold's lead and examined in a JEM-100B microscope.

FIG. 1 shows two typical electron micrographs. As can be seen, each colony is composed of 5–10 flattened cell layers. The electron micrograph shows the stratified appearance of the layers close to the surface in contact with the medium. Tonofilaments and desmosomes are abundant and present in all cell layers. Aggregations of the tonofilaments and the presence of particles resembling keratohyalin granules, generally more striking in the outer cell layers, can also be observed.

EXAMPLE 4

Effect of Ratio of 3T3 Cells to XB Cells on Growth and Keratinization

Cultures varying the ratio between irradiated 3T3 cells and XB cells were carried out following the procedures of Example 3. The results were:

| No. of XB Cells | No. of 3T3 Cells | Growth of Colonies | Keratinization |
| --- | --- | --- | --- |
| 150 | $10^6$ | Yes, but colonies remained very small | Yes |
|  | $3 \times 10^5 (n/3)$ | Yes, much greater lateral expansion | Yes |
|  | $10^5$ | Yes | Optimal |
|  | $3 \times 10^4$ | Yes | Virtually None |
|  | $10^4$ | Yes | None |
|  | 0 | No | No |
| $10^3$ | $3 \times 10^5$ | Yes | Good |
| $10^4$ | $3 \times 10^5$ | Yes | None |
| $10^5$ | $3 \times 10^5$ | Yes | None |

EXAMPLE 5
Growth of XB Cells in Medium Containing 3T3 Cells Located Away From XB Cells $3 \times 10^5$ 3T3 cells were inoculated into a tilted dish and allowed to attach to the lower third. XB cells were then inoculated into the righted dish and permitted to grow. Keratinizing colonies developed on the bare surface of the dish even at a considerable distance from the 3T3 cells. Colony formation took place within the 3T3 layer but the colonies remained small, owing to the high density of the 3T3 cells. Thus, growth and keratinization of XB cells can be supported by the 3T3 cells located some distance away.

EXAMPLE 6
Growth of XB Cells in Medium Conditioned with Fibroblasts

Conditioned medium was prepared by incubating saturation density cultures of unirradiated 3T3 cells for 1 day with medium containing 30% fetal calf serum. The medium was then removed, passed through a nitrocellulose membrane filter and then used either directly or after dilution with 20% of its volume of fresh, serum-free medium. Dishes were inoculated with 200 XB cells in regular medium, and the following day the conditioned medium was substituted. Cultures were refed with conditioned medium once weekly. Colonies formed with an efficiency of about 20% and by 2½ to 3 weeks were as large and well stratified as if they had grown in the presence of n/3 3T3 cells. Most colonies stained well with Rhodamine B.

Conditioned media prepared from other lines in the same way were tested for their ability to support colony formation and keratinization by XB cells. The results, where keratinization is rated on a graded scale from (+) to (+++), were:

| Conditioning Cell Line | Colonies Formed | Intensity of Rhodamine Staining |
| --- | --- | --- |
| None | None |  |
| 3T3 | Large | +++ |
| SB | Large | ++ |
| L5178$_y$ | Small | None |
| X$_{LD}$-1 | Small | None |
| HTC | Minute | + |
| HeLa | None |  |
| H4IIEC$_3$ | None |  |
| ep-1 | None |  |

SB, a strain of fetal human fibroblasts, supported both colony formation and keratinization by the XB cells. None of the media conditioned by other cell lines tested gave comparable results. Medium harvested from cultures of L5178y, a mouse lymphoma line, and X$_{LD}$-1, a nonkeratinizing teratoma line, supported the formation of small colonies of XB cells but the colonies did not stratify or stain with Rhodamine. Medium conditioned by HTC cells (a liver cell line) supported the formation of only minute colonies, but these did stain with Rhodamine. Medium from cultures of HeLa, H4IIEC$_3$ (a hepatoma line) and ep-1 (a nonkeratinizing teratoma line of epithelial appearance) did not support colony formation. Of the lines tested, the fibroblast lines were the only ones able to effectively condition the medium for both growth and keratinization.

EXAMPLE 7
Radioautography Studies

Radioautography studies of sections through large colonies (>1,000 cells) were made after labelling for 20 hours with H$^3$-thymidine (0.5$\mu$Ci/ml). These showed that many nuclei had incorporated the thymidine. The nuclei which did not label were usually located in the most superficial layers of the most stratified part of the colony and were often flattened. The conversion of the keratinocyte to a nondividing and differentiated end stage cell in the colony therefore tends to follow the pattern resembling a stratified squamous epithelium in vivo.

EXAMPLE 8
Frequency of Keratinocyte Colonies in Primary Platings of the Transplanted Teratoma Three experiments were carried out using the culturing and Rhodamine B staining procedures of Example 3. The results were:

| | | Total Colony-Forming Cells (Fraction of Cells Plated) | Colonies with XB-like Morphology | | | |
| --- | --- | --- | --- | --- | --- | --- |
| | | | Nonkeratinized | | Keratinized | |
| Expt. | No. of Cells Plated | | No. of Colonies | Fraction of Total Colonies | No. of Colonies | Fraction of Total Colonies |
| A | $2.2 \times 10^5$ | $2.6 \times 10^{-3}$ | 92 | 0.42 | 10 | $1.7 \times 10^{-2}$ |
| B | $3.3 \times 10^4$ | $8.1 \times 10^{-2}$ | 12 | $4.4 \times 10^{-3}$ | 0 | $<4.0 \times 10^{-3}$ |
| C | $1.8 \times 10^6$ | $4.5 \times 10^{-2}$ | 10 | $1.2 \times 10^{-4}$ | 3 | $3.8 \times 10^{-4}$ |
| TOTAL | $2.0 \times 10^6$ | | 114 | | 13 | |

All yielded numerous colonies of cells resembling the XB cells, but most of these colonies failed to stratify and keratinize. Two of the three experiments did also yield keratinized colonies, which could be identified in the living state. The average frequency of keratinizing colonies for the three experiments was $6 \times 10^{-6}$ per cell plated.

A large fraction of the colonies obtained from the primary platings possessed the appearance of fibroblasts. Of the remaining colonies designated as nonfibroblast, most were not of the keratinocyte type, but they were not identified more precisely. When very numerous, fibroblasts interfered with the development of epithelial colonies, even in the presence of $n/3$ 3T3 cells. With experience the morphology of the living colonies became nearly as reliable as the Rhodamine B staining for identifying keratinization. It is therefore possible to isolate keratinocyte colonies (like XB) from a primary culture of a teratoma and transfer them serially.

EXAMPLE 9

Growth and Keratinization of Human Diploid Epidermal Cells

Skin biopsies from foreskin or other sites were placed aseptically into fortified Eagle's medium containing 10% calf serum, at room temperature. Within 3 hours, most of the subcutaneous tissue could be removed with surgical scissors, and the remaining skin (1–3 cm$^2$ in area) was minced finely with scissors to pieces less than 1 mm in diameter. These were stirred in 10 ml 0.25% trypsin at 37° C. After allowing 1 minute for settling, the supernatant, containing >95% single cells, was withdrawn at 30 minute intervals, and replaced with fresh trypsin solution. The cells were centrifuged, resuspended in medium containing 20% fetal calf serum and hydrocortisone 0.4μg/ml, mixed with lethally irradiated 3T3 cells, and plated. The medium was changed 3 to 5 days later, when most epidermal cells had attached, and twice weekly thereafter until the cells were subcultured or fixed and stained.

In these cultures, the 3T3 cells quickly formed a monolayer on the surface of the dish but the epidermal cells often required several days to attach. These human epidermal keratinocytes eventually made contact with the surface of the dish and grew as expanding colonies on the vessel surface, pushing away the 3T3 feeders at the periphery.

Subcultures were made after removing nearly all 3T3 cells and viable fibroblasts by exposing the culture to 0.02% EDTA for 15 seconds and vigorous pipetting. The keratinocyte colonies, which remained adherent, were then disaggregated to single cells in a solution containing equal parts of EDTA and 0.05% trypsin, and replated together with fresh irradiated 3T3 cells. The keratinocytes were usually subcultured when the average colony size reached about 1,000 cells.

Efficiency of colony formation by keratinocytes was determined by plating 10$^3$ to 10$^5$ cells together with $n/3$ 3T3, fixing 2 to 4 weeks later, and staining with Rhodanile blue. The extent of contamination by human fibroblasts was determied by plating 300 to 10$^4$ cells with $n/30$ 3T3. The cultures were fixed 1 to 2 weeks later and stained with hematoxylin for counts of fibroblast colonies.

The results of serially culturing human diploid epidermal cells from a variety of donors are presented in the Table at the end of this Example.

Vertical sections through the colonies, after staining with hematoxylin and eosin, showed stratified squamous epithelium more regularly oganized than that produced by the XB line. The surface of the colony was more uniform and there were no round cells.

The plating efficiency of human keratinocytes was variable but always considerably lower than that for XB teratomal keratinocytes. The Table illustrates that the number of keratinocyte colonies produced by primary disaggregated skin cells was usually 0.1–1.0%. Since most epidermal cells in skin are probably not capable of division and the biopsies also contain dermal cells, this seems a reasonable value. Yet even on subculture, the plating efficiency was only occasionally as high as 10% and was usually 1–5% even for newborn donors. Toward the end of their culture life the epidermal keratinocytes of both newborn and older donors plated with an efficiency considerably below 1%.

Human epidermal keratinocytes in primary or subsequent culture had a doubling time of about 32 hours over the period from the time of inoculation to the development of colonies containing an average of about 1,000 cells. Since this includes their period of attachment, it is likely that the doubling time in the exponential phase is appreciably shorter. The growth rate of the keratinocytes did not seem to change much on serial subculture until close to the end of their culture life, when it declined sharply.

The keratinocyte strains initiated from humans at different ages from birth to 34 years showed finite culture lifetimes; all grew for at least two transfers, but none grew through more than six.

The number of cell generations could not be obtained from the dilution at each transfer since the plating efficiency was low. The number of colonies initiated at each transfer was estimated from plates inoculated with 10$^3$ to 10$^5$ cells (Table, column II). The final yield of cells from any plate (Table, column IV) was then related to the number of colony forming cells. This gave the number of cell generations grown in each subculture.

These values and the cumulative totals are shown in the Table. It can be seen that of seven cultures initiated from biopsy, the number of cell generations grown was from 20 to 50. These values are likely to be on the low side. After stratification of the colonies, cells in the upper layers do not divide and appear to differentiate toward squame formation; the remaining dividing population would therefore undergo more divisions that would be calculated from the total yield per cell colony.

It is likely that, as in the case of human fibroblasts, the epidermal cells of older donors have reduced growth potential, since keratinocytes of ages 3–34 years grew through a total of 20–27 generations, whereas those from newborns grew through 25–51 generations. The plating efficiency of the keratinocytes of older donors was always less than 1%, whereas that of newborns was often in the range of 2–10% (Table, column II). It is also possible that the side of origin of the keratinocytes has some bearing on their behavior in culture, for the keratinocytes of the two oldest donors were derived from abdominal skin while the others were derived from foreskin.

The minimum number of generations through which the keratinocytes grew in culture, 20 cell generations, corresponds to an increase in cell mass of approximately 10$^6$ fold if all progeny could initiate colony formation, but in view of the low plating efficiency on subculture, such increases in cell mass were not actually obtained. It is therefore useful to calculate the actual expansion of the keratinocyte population in the course of serial cultivation, without correcting for the losses due to low plating efficiency. The Table shows that the values varied from 2.6 to over $10^4$ fold. The median value was 600 fold. It is quite likely that improvement of culture conditions will result in an increased plating efficiency and thereby permit greater expansion of the keratinocyte populations.

EXAMPLE 10

Radioautography Studies

Radioautography was carried out on colonies containing over 1,000 cells by adding labelled thymidine to the medium of cultures for 24 hours (tritiated, 0.5$\mu$Ci/ml (50 Ci/mmole); $C^{14}$, 5$\mu$Ci/ml (54 mCi/mmole)). The medium was then removed and a solution of 0.5% NP40 was added. Two minutes later the 3T3 cells were dislodged. The keratinocyte colonies remained attached but the cytoplasmic compartments

| | | | | | Serial Cultivation of Human Keratinocyte Strains in Culture | | | | |
|---|---|---|---|---|---|---|---|---|---|
| | | | | | Colonies per 100 Cells | | | | No. of |
| | Age | | | Inoculum | Inoculated | | Keratinocyte Yield | | Generations |
| Strain | of Donor | Date Plated | Passage No. | (Cells) I | Keratinocyte II | Fibroblast III | Cells IV | Colonies V | This Passage | Cumulative |
|---|---|---|---|---|---|---|---|---|---|---|
| HFE | n | 9/10/74 | 1 | $10^5$ | 0.7 | | $10^6$ | 700 | 10.4 | 10.4 |
| | | 9/24/74 | 2 | $5 \times 10^4$ | 5 | | $3.8 \times 10^6$ | 2500 | 10.3 | 20.7 |
| | | 10/04/74 | 3 | $10^5$ | 2 | | $2.0 \times 10^6$ | 2000 | 10 | 30.7 |
| | | 10/15/74 | 4 | $10^5$ | 0.3 | | $2.0 \times 10^4$ | 300 | 6 | 36.7 |
| | | expansion of keratinocyte population in culture: $1.5 \times 10^4$ fold | | | | | | | | |
| HFE (f) | n | 1/09/75 | 1 | $3 \times 10^4$ | 0.8 | 0.04 | $2.6 \times 10^5$ | 240 | 10 | 10 |
| | | 1/24/75 | 2 | $10^5$ | 2.5 | 0.7 | $1.4 \times 10^6$ | 2500 | 9 | 19 |
| | | 2/07/75 | 3 | $5 \times 10^5$ | 1.8 | >10 | $2.6 \times 10^6$ | 9000 | 8 | 27 |
| | | expansion of keratinocyte population in culture: 626 fold | | | | | | | | |
| A | n | 2/11/75 | 1 | $5 \times 10^5$ | 0.9 | 0.8 | $3.8 \times 10^6$ | 4500 | 10 | 10 |
| | | 2/24/75 | 2 | $3 \times 10^5$ | 2.3 | 1.0 | $2.5 \times 10^6$ | 6900 | 9 | 19 |
| | | 3/06/75 | 3 | $10^5$ | 0.6 | 1.6 | $7.0 \times 10^5$ | 600 | 10 | 29 |
| | | 3/21/75 | 4 | $2 \times 10^5$ | 0.14 | >10 | c | 287 | ~9$^a$ | ~38 |
| | | expansion of keratinocyte population in culture: 442 fold | | | | | | | | |
| B | n | 2/11/75 | 1 | $5 \times 10^5$ | 2.8 | 1.8 | $2.7 \times 10^6$ | 14000 | 8 | 8 |
| | | 2/24/75 | 2 | $2 \times 10^5$ | 1.7 | 6.5 | $8.4 \times 10^5$ | 3000 | 8 | 16 |
| | | 3/06/75 | 3 | $10^5$ | 0.2 | 4.7 | $10^5$ | 200 | 9 | 25 |
| | | 3/21/75 | 4 | $10^5$ | c | 28 | c | | | |
| | | expansion of keratinocyte population in culture: 23 fold | | | | | | | | |
| C | n | 4/04/75 | 1 | $10^5$ | 0.04 | 0.2 | $2.7 \times 10^5$ | 40 | 12.5 | 12.5 |
| | | 4/24/75 | 2 | $10^5$ | 3.6 | 0.27 | $1.3 \times 10^6$ | 3600 | 8.5 | 21 |
| | | 5/08/75 | 3 | $2 \times 10^5$ | 7.5 | 0.2 | $2.5 \times 10^6$ | 15000 | 7.5 | 28.5 |
| | | 5/21/75 | 4 | $3 \times 10^5$ | 0.7 | 0.1 | $2.6 \times 10^5$ | 2100 | 7 | 35.5 |
| | | 6/05/75 | 5 | $1.1 \times 10^5$ | 0.5 | 1.2 | $3.7 \times 10^5$ | 550 | 9.5 | 45 |
| | | 6/17/75 | 6 | $2 \times 10^5$ | 0.55 | | c | 1100 | 6$^a$ | 51 |
| | | expansion of keratinocyte population in culture: 1500 fold | | | | | | | | |
| E (f) | n | 4/24/75 | 1 | $10^5$ | 0.15 | 0.12 | $1.4 \times 10^5$ | 150 | 10 | 10 |
| | | 5/08/75 | 2 | $10^5$ | 8.2 | 0.1 | $6.0 \times 10^5$ | 8200 | 6 | 16 |
| | | 5/17/75 | 3 | $10^5$ | 10.0 | | $5.8 \times 10^5$ | 10000 | 6 | 22 |
| | | 5/27/75 | 4 | $2 \times 10^5$ | 4.8 | 0.5 | $4.6 \times 10^5$ | 9600 | 6 | 28 |
| | | 6/04/75 | 5 | $1.5 \times 10^5$ | 2.0 | 0.2 | $7.5 \times 10^5$ | 3000 | 8 | 36 |
| | | 6/17/75 | 6 | $2 \times 10^5$ | 0.5 | <0.1 | c | 1000 | 9$^a$ | 45 |
| | | expansion of keratinocyte population in culture: 560 fold | | | | | | | | |
| E (f) repeat | n | 4/24/75 | 1 | $10^5$ | 0.15 | 0.12 | $1.5 \times 10^5$ | 150 | 10 | 10 |
| | | 5/10/75 | 2 | $5 \times 10^4$ | 15.7 | <0.1 | $1.5 \times 10^6$ | 7850 | 8 | 18 |
| | | 5/21/75 | 3 | $3 \times 10^5$ | 3.3 | <0.1 | $2.3 \times 10^6$ | 10000 | 8 | 26 |
| | | 6/04/75 | 4 | $10^5$ | 1.8 | 0.2 | $5.1 \times 10^5$ | 1800 | 8 | 34 |
| | | 6/17/75 | 5 | $10^5$ | 1.2 | 0.4 | $3.7 \times 10^5$ | 1200 | 8 | 42 |
| | | 6/30/75 | 6 | $3 \times 10^4$ | 0.6 | 1.3 | $10^5$ | 180 | 9 | 51 |
| | | expansion of keratinocyte population in culture: $2.2 \times 10^4$ fold | | | | | | | | |
| GRE | 3 yrs. | 2/10/75 | 1 | $10^4$ | 0.45 | 5 | $5.6 \times 10^4$ | 45 | 10 | 10 |
| | | 2/25/75 | 2 | $2 \times 10^4$ | 0.3 | 0.25 | $1.6 \times 10^5$ | 60 | 11.5 | 21.5 |
| | | 3/21/75 | 3 | $1.4 \times 10^5$ | 0.007 | 1.8 | c | 10 | ~5$^a$ | 26.5 |
| | | expansion of keratinocyte population in culture: 45 fold | | | | | | | | |
| HAE | 12 yrs | 10/25/74 | 1 | $3 \times 10^4$ | 0.7 | | $1.1 \times 10^6$ | 200 | 12.5 | 12.5 |
| | | 11/08/74 | 2 | $10^4$ | 0.15 | | $2.6 \times 10^5$ | 150 | 10.5 | 23.0 |
| | | expansion of keratinocyte population in culture: 952 fold | | | | | | | | |
| CS-1 | 34 yrs | 4/16/75 | 1 | $3 \times 10^5$ | 0.1 | <0.01 | $3.8 \times 10^5$ | 300 | 10.5 | 10.5 |
| | | 5/08/75 | 2 | $10^5$ | 0.3 | 0.4 | $2.2 \times 10^5$ | 300 | 9.5 | 20 |
| | | expansion of keratinocyte population in culture: 2.6 fold | | | | | | | | | n — newborn
(f) — cultures initiated from suspensions of trypsin-disaggregated cells stored viably in the frozen state.
II — estimated from cultures inoculated with $10^3 - 10^5$ cells together with n/3 3T3.
III — estimated from cultures inoculated with 300 – $10^4$ cells together with n/30 3T3.
IV — cell layers were treated with EDTA for 20 seconds, and the 3T3 cells and human fibroblasts were dislodged by vigorous pipetting and aspirated. The remaining cells were then removed with trypsin-EDTA and counted (any residual 3T3 cells were not included — see Experimental Procedures).
V — calculated from values in columns I and II. Expansion of keratinocyte populations in culture were obtained as the product of the increases at each passage listed in columns I and IV.
$^a$ — estimated from average colony size.
c — indeterminate because of excessive fibroblast growth.

became substantially emptied and the nuclei became easily visible. The cultures were then fixed, stained, dried and covered with photographic emulsion. After 5–10 days the emulsion was developed.

Radioautography showed that the nuclei close to the perimeter of the colonies produced abundant grains but those in the interior of the colonies showed very faint grain density or none at all. When the same cultures were labelled with $C^{14}$-thymidine, many nuclei in the internal regions of the colonies were labelled. These nuclei were presumably so deep within the colony that $\beta$ particles emitted from tritium could not reach the emulsion; but even after exposure to $C^{14}$-thymidine unlabelled nuclei could be seen in large flattened cells with thickened cell membranes in the superficial layers of the thicker colonies. These nuclei appeared to belong to cells in the process of differentiation into squames. Radioautographs of cross sections of large colonies labelled with tritiated thymidine showed that in areas where stratification had occurred, no labelled nuclei were present in the upper layers.

EXAMPLE 11

Electron Micrographs

Electron micrographs of sections through colonies confirmed the stratified construction, the keratinization (most advanced in the upper cell layers) and the abundant desmosomes in all layers. FIG. 2 is a typical electron micrograph, and as can be seen, the appearance resembles that of epidermis, and all the cells belong to the same type — keratinocytes. Though they are flattened, the cells closest to the petri dish surface correspond most closely to the germinative cells in normal epidermis, for cell division in stratified colonies takes place mainly in the deeper layers.

EXAMPLE 12

Chromosome Complement of the Epidermal Cells

In order to examine the chromosomes of the human epidermal keratinocytes, it was necessary to obtain the cells completely free of human fibroblasts. This was accomplished by plating primary disaggregated foreskin cells in such number as to yield about three epidermal colonies per plate. A colony was isolated, trypsinized and transferred to dishes containing $n/3$ and $n/30$ 3T3. The purity of the isolated colony was confirmed by the absence of fibroblast colonies on the $n/30$ monolayer. Epidermal cells growing on the $n/3$ layers were treated with colchicine ($2 \times 10^{-6}$M) for 2 hours and metaphase preparations were made by conventional methods and stained with orcein. In spite of their large dose of irradiation, abnormal 3T3 metaphases were often seen, but these were easily identified. Well spread human metaphases were counted and found to have the diploid number of chromosomes.

EXAMPLE 13

Dependence of Human Diploid Epithelial Cell Growth on Presence of Fibroblast Cells Cultures of human diploid epithelial cells were attempted following the procedures of Example 9 but eliminating the presence of fibroblasts. All attempts produced no colony formation.

EXAMPLE 14

Effect of Varying Fibroblast Cell Density on the Ability of Human Epidermal Keratinocytes to Form Colonies Cultures were prepared following the procedures of Example 9 but varying the 3T3 cell density. The results were:

| No. of Keratinocytes Plated | No. of 3T3 Cells Plated | No. of Keratinocyte Colonies Formed | Keratinization |
|---|---|---|---|
| $10^4$ | $10^6(n)$ | 600 | + |
| $10^4$ | $3 \times 10^5(n/3)$ | 600 | + |
| $10^4$ | $1.5 \times 10^5(n/6)$ | 240 | + |
| $10^4$ | $7.5 \times 10^4(n/12)$ | 90 | + |
| $10^4$ | $3.8 \times 10^4(n/24)$ | 3 | + |

EXAMPLE 15

Effect of Previous Growth with EGF on the Colony Forming Efficiency of Human Epidermal Keratinocytes $10^4$ human epidermal keratinocytes were plated with an $n/3$ x-3T3 fibroblast layer in the presence or absence of 30 ng/ml EGF and the growth and colony forming efficiency of the keratinocytes was measured at 2 or 3 day intervals. The results of the presence (+) or absence (−) of EGF on efficiency of plating (e.o.p.) were determined to be:

| Strain | No. of Gens. at plating | Grown ± EGF and e.o.p. (%) at Next Passage | | | | |
|---|---|---|---|---|---|---|
| | | Passage 1 | Passage 2 | Passage 3 | Passage 4 | Passage 5 |
| HFE | 10 | − | 2.5 | | | |
| | 19 | − | − | 1.8 | | |
| | 27 | − | − | − | 0.3 | |
| | 11 | + | 12.5 | | | |
| | 19 | + | + | 9.0 | | |
| | 27 | + | + | + | 3.0 | |
| | 39 | + | + | + | + | 0.3 |

It can be seen that EGF prolonged culture life and increased plating efficiency.

EXAMPLE 16

Effect of EGF on Rate of Growth and Colony Forming Ability of Human Epidermal Keratinocytes Cultured with $n/3$ x-3T3

Human epidermal keratinocyte strains were cultured with an $n/3$ x-3T3 feeder layer in the presence or absence of 30 ng/ml EGF, and colony forming ability and cell yield were measured. As can be seen from the data, EGF increased both cell growth and colony forming ability. The results were:

| Strain (No. of Gens.) | No. of Colonies Per Culture | Days After Plating | −EGF | | +EGF | | +EGF/−EGF | |
|---|---|---|---|---|---|---|---|---|
| | | | Cell Number | e.o.p. of Cells (%) | Cell Number | e.o.p. of Cells (%) | Cell Number | e.o.p. of Cells (%) |
| E (21) | 950 | 6 | $2.0 \times 10^4$ | 6.0 | $1.5 \times 10^4$ | 13.2 | 0.8 | 2.2 |
| | | 9 | $1.3 \times 10^5$ | — | $2.6 \times 10^5$ | — | 2.0 | — |
| | | 11 | $4.5 \times 10^5$ | 0.7 | $1.5 \times 10^6$ | 4.5 | 3.3 | 6.4 |
| | | 13 | $5.0 \times 10^5$ | 1.3 | $2.2 \times 10^6$ | 11.5 | 4.4 | 8.8 |
| | | 15 | $6.5 \times 10^5$ | 2.2 | $3.3 \times 10^6$ | 6.1 | 5.1 | 2.8 |
| | | 17 | $1.0 \times 10^6$ | — | $3.2 \times 10^6$ | — | 3.2 | — |

Those skilled in the art will recognize that there are many equivalents to the specific embodiments described herein. For example, epidermal-like cells other than the human epidermal or teratoma XB cells actually used in the Examples are suitable as long as they can be serially cultured according to the techniques described herein. Similarly, those skilled in the art will recognize that fibroblasts other than 3T3 and SB are suitable for use in supporting epidermal cell growth and keratinization. Also, the specific techniques, such as that used to prevent fibroblast multiplication, have equivalents. These equivalents are intended to be covered by the following claims.

What is claimed is:

1. In the growth of keratinocytes in culture, the improvement of including in said culture either fibroblast cells treated to prevent their multiplication and at a density sufficient for keratinocyte multiplication, differentiation and colony expansion or medium conditioned by fibroblast cells.

2. An improvement of claim 1 wherein said culture contains 3T3 mouse fibroblast cells treated to prevent their multiplication.

3. An improvement of claim 2 wherein said 3T3 mouse fibroblast cells are treated to prevent their multiplication by irradiating them with ionizing radiation.

4. A method for serially culturing keratinocytes, comprising:
   a. forming a culture containing keratinocytes and either (1) fibroblast cells treated to prevent their multiplication and at a density sufficient to allow keratinocyte colonies to grow, or (2) medium sufficiently conditioned by fibroblast cells to allow keratinocyte colonies to grow;
   b. maintaining said culture under conditions conductive to cell growth whereby keratinocyte colonies are formed;
   c. harvesting said keratinocyte colonies; and,
   d. serially replating said keratinocyte colonies into subculture.

5. A method of claim 4 wherein said culture contains fibroblast cells treated to prevent their multiplication, said treated cells being present at a density sufficient to allow keratinocyte colonies to grow.

6. A method of claim 5 wherein said keratinocytes comprise human epidermal cells.

7. A method of claim 6 wherein said fibroblast cells comprise 3T3 mouse fibroblast cells.

8. A method of claim 7 wherein said 3T3 mouse fibroblast cells have been irradiated with ionizing radiation to prevent their multiplication.

9. A method of claim 8 wherein said human epidermal cells are inoculated at a density of from about 50 to about 50,000 cells/cm$^2$.

10. A method of claim 9 wherein said 3T3 mouse fibroblast cells are inoculated at a density from about 15,000 to about 50,000 cells/cm$^2$.

11. A method of claim 7 wherein said culture also contains from about 1 to about 30 nanograms/ml of epidermal growth factor.

12. A method of claim 10 wherein said culture also contains from about 1 to about 30 nanograms/ml of epidermal growth factor.

13. A method of claim 7 wherein said culture also contains from about 0.03 to about 10 micrograms/ml of hydrocortisone.

14. A method of claim 12 wherein said culture also contains from about 0.03 to about 10 micrograms/ml of hydrocortisone.

15. A method of claim 14 wherein said culture contains Eagle's medium.

16. A method of claim 14 wherein said culture contains Eagle's medium supplemented with about 20% fetal calf serum.

17. A method of claim 4 wherein said keratinocytes comprise teratomal keratinocytes.

18. A method of claim 17 wherein said culture contains medium sufficiently conditioned by fibroblast cells to allow keratinocyte colonies to grow.

19. A method of claim 17 wherein said culture contains fibroblast cells treated to prevent their multiplication and at a density sufficient to allow keratinocyte colonies to grow.

20. A method of claim 19 wherein said teratomal keratiocytes comprise mouse teratomal keratinocytes.

21. A method of claim 20 wherein said fibroblast cells comprise 3T3 mouse fibroblast cells.

22. A method of claim 21 wherein said 3T3 mouse fibroblast cells have been irradiated with ionizing radiation to prevent their multiplication.

23. A method of claim 22 wherein said moiuse teratomal cells comprise clonal XB cells.

24. A method of claim 23 wherein said clonal XB cells are inoculated at a density of up to about 50 cells/cm$^2$.

25. A method of claim 24 wherein said irradiated 3T3 mouse fibroblast cells are inoculated at a density of up to about 15,000 cells/cm$^2$.

26. A Cell culture comprising an isolated clonal cell line derived from a culture of mouse teratomal cells, said clonal cell line having the ability to form keratinized stratified, squamous epithelium upon serial cultivation and a suitable cell culture medium therefor.

27. A cell culture comprising ATCC CL-177 cells in a suitable medium therefor.

* * * * *

UNITED STATES PATENT AND TRADEMARK OFFICE
CERTIFICATE OF CORRECTION

PATENT NO. : 4,016,036

DATED : April 5, 1977

INVENTOR(S) : Howard Green, Brookline; James G. Rheinwald, Cambridge, both of Mass.

It is certified that error appears in the above-identified patent and that said Letters Patent are hereby corrected as shown below:

Claim 9, line 3, change "50,000" to ---5,000---.

Signed and Sealed this

Twenty-second Day of August 1978

[SEAL]

Attest:

RUTH C. MASON
Attesting Officer

DONALD W. BANNER
Commissioner of Patents and Trademarks